US011769229B2

United States Patent
Gong et al.

(10) Patent No.: US 11,769,229 B2
(45) Date of Patent: Sep. 26, 2023

(54) SYSTEMS AND METHODS FOR REAL-TIME VIDEO DENOISING

(71) Applicant: Subtle Medical, Inc., Menlo Park, CA (US)

(72) Inventors: Enhao Gong, Sunnyvale, CA (US); Ben Andrew Duffy, Palo Alto, CA (US); Gajanana Keshava Datta, Los Altos, CA (US); David Van Veen, San Francisco, CA (US)

(73) Assignee: Subtle Medical, Inc., Menlo Park, CA (US)

( * ) Notice: Subject to any disclaimer, the term of this patent is extended or adjusted under 35 U.S.C. 154(b) by 0 days.

(21) Appl. No.: 18/052,411

(22) Filed: Nov. 3, 2022

(65) Prior Publication Data
US 2023/0121890 A1   Apr. 20, 2023

Related U.S. Application Data

(63) Continuation of application No. PCT/US2022/032337, filed on Jun. 6, 2022.
(Continued)

(51) Int. Cl.
*G06T 5/00* (2006.01)
*G06T 5/50* (2006.01)
*G06T 7/20* (2017.01)

(52) U.S. Cl.
CPC ............ *G06T 5/002* (2013.01); *G06T 5/50* (2013.01); *G06T 7/20* (2013.01);
(Continued)

(58) Field of Classification Search
CPC .. G06T 5/002; G06T 5/50; G06T 7/20; G06T 2207/10121; G06T 2207/20182;
(Continued)

(56) References Cited

U.S. PATENT DOCUMENTS 6,023,303 A    2/2000  Kagawa
8,384,787 B2 *  2/2013  Wu ................... H04N 23/6811
                                                 348/208.6
(Continued)

FOREIGN PATENT DOCUMENTS

CN    103177423 A  *  6/2013  ............ G06T 5/002
CN    110610467 A  *  12/2019  ........... G06N 3/0454
(Continued)

OTHER PUBLICATIONS

Chan et al., "Image Sequence Filtering in Quantum-Limited Noise with Applications to Low-Dose Fluoroscopy", IEEE Trans. Medical Imaging, vol. 12, issue 3, pp. 610-621, Sep. 1993. (Year: 1993).*
(Continued)

*Primary Examiner* — Jose L Couso
(74) *Attorney, Agent, or Firm* — Wilson Sonsini Goodrich & Rosati

(57) ABSTRACT

A computer-implemented method is provided for improving live video quality. The method comprises: (a) acquiring, using a medical imaging apparatus, a stream of consecutive image frames of a subject; (b) feeding the stream of consecutive image frames to a first set of denoising components, wherein each of the first set of denoising components is configured to denoise an image frame from the stream of consecutive image frames in a spatial domain to output an intermediate image frame; (c) feeding a plurality of the intermediate image frames to a second denoising component, wherein the second denoising component is configured to (i) denoise the plurality of the intermediate image frames in a temporal domain and (ii) generate a weight map; and outputting a final image frame with improved quality in both temporal domain and spatial domain based at least in part on the weight map.

20 Claims, 9 Drawing Sheets

Related U.S. Application Data

(60) Provisional application No. 63/212,267, filed on Jun. 18, 2021.

(52) U.S. Cl.
CPC ............... *G06T 2207/10121* (2013.01); *G06T 2207/20182* (2013.01); *G06T 2207/20221* (2013.01)

(58) Field of Classification Search
CPC ........... G06T 2207/20221; G06T 5/003; G06T 2207/10016; G06T 2207/30004; G06T 3/4046; G06T 9/002; G06T 2207/20076; G06T 2207/20081; G06T 2207/20084; H04N 19/577; H04N 5/144; H04N 5/145; H04N 19/51; G06V 10/30; G06V 2201/03; G06V 20/40; G06V 10/454; G06V 10/54; G06V 10/774; G06V 10/82; G06V 30/18057; A61B 6/486; A61B 6/487; A61B 6/5258; A61B 8/5269; A61B 8/5256; A61B 8/5264; A61B 8/5276; G06N 3/02; G06N 3/08–088; G06N 3/0445; G06N 3/0454; G06N 3/4046; G06N 7/00; G06N 20/00; G06K 7/1482; Y10S 128/925

See application file for complete search history.

(56) References Cited

U.S. PATENT DOCUMENTS

| | | | |
|---|---|---|---|
| 2007/0206117 A1 | 9/2007 | Tian et al. | |
| 2007/0274605 A1 | 11/2007 | Yahil | |
| 2013/0089247 A1* | 4/2013 | Mercuriev | G06T 5/002 382/128 |
| 2013/0321286 A1 | 12/2013 | Petruzzelli et al. | |
| 2013/0329135 A1 | 12/2013 | Baqai et al. | |
| 2014/0219531 A1* | 8/2014 | Epstein | G06T 7/20 382/131 |
| 2017/0278225 A1* | 9/2017 | Nishimura | G06T 5/50 |
| 2018/0053300 A1* | 2/2018 | Podilchuk | G06T 7/0016 |
| 2019/0333199 A1* | 10/2019 | Ozcan | G06T 3/4046 |
| 2020/0364834 A1* | 11/2020 | Ferrés | H04N 23/683 |
| 2021/0000369 A1* | 1/2021 | Luksic | A61B 34/20 |
| 2021/0049795 A1* | 2/2021 | Cao | G06T 7/11 |
| 2022/0117508 A1* | 4/2022 | Dharmakumar | A61B 5/145 |
| 2022/0373630 A1* | 11/2022 | Dou | G01R 33/56509 |

FOREIGN PATENT DOCUMENTS

| | | | | |
|---|---|---|---|---|
| CN | 110852961 A | * | 2/2020 | ............ G06T 5/002 |
| CN | 112801887 A | * | 5/2021 | ............ G06T 5/002 |
| WO | WO-2015049103 A1 | * | 4/2015 | ............ G06T 5/002 |
| WO | 2021163022 A1 | | 8/2021 | |

OTHER PUBLICATIONS

Aufrichtig et. al., "X-Ray Fluoroscopy Spatio-Temporal Filtering with Object Detection", IEEE Trans. Medical Imaging 14 (Dec. 13, 1995) pp. 733-746. (Year: 1995).*

Harris, M., "CUDA Pro Tip: Increase Application Performance with NVIDIA GPU Boost", Internet article on a technical blog, pp. 1-2, Mar. 19, 2014. (Year: 2014).*

Printout of Internet search on Google search for "NVIDIA.RTM" on Mar. 23, 2023 10:42am, pp. 1-3. (Year: 2023).*

Tassano, et al., "Fastdvdnet: Towards Real-Time Deep Video Denoising Without Flow Estimation," Proceedings of the IEEE/CVF Conference on Computer Vision and Pattern Recognition, 2020. Retrieved on Sep. 18, 2022. <https://openaccess.thecvf.com/content_CVPR_2020/html/Tassano_FastDVDnet_Towards_Real-Time_Deep_Video_Denoising_Without_Flow-Estimation_CVPR_2020_paper.html>.

Tassano, et al., "DVDnet: A fast network for deep video denoising." 2019 IEEE International Conference on Image Processing (ICIP). IEEE, 2019.

Tassano, et al., "FastDVDnet: Towards Real-Time Deep Video Denoising Without Flow Estimation." Proceedings of the IEEE/CVF Conference on Computer Vision and Pattern Recognition. 2020.

Claus, et al., "Videnn: Deep blind video denoising." Proceedings of the IEEE Conference on Computer Vision and Pattern Recognition Workshops. 2019.

* cited by examiner

SYSTEMS AND METHODS FOR REAL-TIME VIDEO DENOISING

CROSS-REFERENCE TO RELATED APPLICATION

This application is a continuation of International Application No. PCT/US2022/032337, filed Jun. 6, 2022, which claims priority to U.S. Provisional Application No. 63/212,267 filed on Jun. 18, 2021, the content of which is incorporated herein in its entirety

BACKGROUND

Image-guided surgery systems have been utilized to inspect patient anatomy or guide surgical instruments during surgical operations. These vision or image-guided systems may provide real-time vision feedback of the surgeon's movements, target site location, and various other useful information which can be displayed in real-time on computer monitors in the operating room or remotely.

Various imaging modality (e.g., ultrasound, fluoroscopic imaging, computed tomography (CT), magnetic resonance imaging (MRI), C-arm fluoroscopy, etc.) may provide in vivo real-time imaging. For example, fluoroscopy imaging and other imaging systems may be provided to intraoperative interactive surgery planning and display systems, mixing live video of the external surface of the patient with interactive computer-generated models of internal anatomy obtained from medical diagnostic imaging data of the patient. The computer images and the live video are coordinated and displayed to a surgeon in real time during surgery, allowing the surgeon to view internal and external structures and the relationship between them simultaneously, and adjust the surgery accordingly. This may allow for safer and less invasive procedures as the surgeons have greater control of the procedure, hence reducing tissue trauma and disruption.

However, fluoroscopic imaging relies on ionizing radiation to provide physicians with high quality video feedback during surgical operation. Radiation exposure is harmful for both physicians and patients, but reducing dosage can result in a noisier video. Additionally, blurring or artifacts due to motion may occur during a lengthy scanning. Conventional video denoising algorithms may employ mechanisms for motion compensation. For example, optical flow can be estimated and used to warp neighboring frames into the same space. However, current denoising approaches can result in blurring, artifacts and a reduction in spatial and temporal resolution.

SUMMARY

Methods and systems are provided for enhancing quality of live video. In particular, the present disclosure may provide an improved video denoising method allowing for spatiotemporal motion resilient video denoising. Denoising may be applied to both spatial and temporal domain. The methods and systems provided herein may address various drawbacks of conventional systems, including those recognized above. Methods and systems of the present disclosure may be capable of improving live video quality in real-time by reducing the noise dynamically adapting to the motion in the video by varying the degree of spatial denoising, temporal denoising or a combination of both. This may beneficially improve operation safety to both patient and surgeon, as well as allow for long duration surgical operations (e.g., interventional procedures such as placing stents or other devices inside the body may which require fluoroscopy be administered for a long period of time).

The provided methods and systems may improve live video/imaging quality by employing deep learning techniques so as to reduce noise. Due the complex computation, the runtime at inference for conventional deep-learning based denoiser can be high rendering denoising can only be performed off-line or with a time delay. Methods or algorithms herein may improve live imaging quality with reduced/decreased inference runtime. This beneficially allows for real-time video enhancement that was not previously available due to the high inference runtimes of the conventional denoiser. Various video artifacts such as temporal artifacts (e.g., visible flickering), image artifacts such as noise (e.g., low signal noise ratio), blur (e.g., motion artifact), shading (e.g., blockage or interference with sensing), missing information (e.g., missing pixels or voxels in painting due to removal of information or masking), and/or reconstruction (e.g., degradation in the measurement domain) may be mitigated by the provided methods and systems.

The provided method and systems are applicable to various imaging modalities. Methods and systems of the disclosure may be applied to existing systems without a need of a change of the underlying infrastructure. In particular, the provided methods and systems may improve live imaging at no additional cost of hardware component and can be deployed regardless of the configuration or specification of the underlying infrastructure.

In an aspect, a computer-implemented method is provided for improving live video quality. The method comprises: acquiring, using a medical imaging apparatus, a stream of consecutive image frames of a subject; feeding the stream of consecutive image frames to a first set of denoising components, where each of the first set of denoising components is configured to denoise an image frame from the stream of consecutive image frames in a spatial domain to output an intermediate image frame; and feeding a plurality of the intermediate image frames to a second denoising component. The second denoising component is trained to (i) predict a motion map indicating a presence of motion in the plurality of the intermediate image frames and (ii) outputting a final image frame with improved quality in both temporal domain and spatial domain based at least in part on the predicted motion map.

In a related yet separate aspect, a system is provided for improving live video quality. The system comprises: (i) a communication interface communicatively coupled to a medical imaging apparatus, (ii) a memory for storing a set of software instructions, and (iii) one or more processors configured to execute the set of software instructions to: receive, from the medical imaging apparatus, a stream of consecutive image frames of a subject; feed the stream of consecutive image frames to a first set of denoising components, where each of the first set of denoising components is trained to denoise an image frame from the stream of consecutive image frames in a spatial domain to output an intermediate image frame; and feed a plurality of the intermediate image frames to a second denoising component. The second denoising component is trained to (i) predict a motion map indicating a presence of motion in the plurality of the intermediate image frames and (ii) outputting a final image frame with improved quality in both temporal domain and spatial domain based at least in part on the predicted motion map.

In some embodiments, the second denoising component is an integrated multi-task network trained to predict the motion map and perform temporal or spatiotemporal denoising. In some embodiments, the second denoising component comprises a separate network trained to predict the motion map.

In some embodiments, the method further comprises combining of the plurality of intermediate image frames and a denoised image frame generated by the second denoising component using the motion map to output the final image frame. In some embodiments, the motion map is a binary map and has a spatial resolution same as the intermediate image frame. In some cases, a value of a pixel in the motion map indicates whether to perform temporal or spatiotemporal denoising to the pixel.

In some embodiments, a number of the stream of consecutive image frames are adjustable. In some embodiments, the medical imaging apparatus is performing fluoroscopic imaging. In some embodiments, the stream of consecutive image frames is acquired with a reduced amount of radiation dose.

In some embodiments, each of the first set of denoising components and second denoising component includes a modified U-net model. In some embodiments, the first set of denoising components are trained using training datasets comprising a pair of a simulated low-quality video and a simulated high-quality video. In some cases, the simulated low-quality video comprises a motion of an object. In some cases, the pair of the simulated low-quality video and the simulated high-quality video are generated from a video acquired at a standard amount of radiation dose. In some instances, the simulated low-quality video is generated by introducing a selected type of artifact or a simulated noise at a selected level to the video acquired at the standard amount of radiation dose.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and descriptions are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
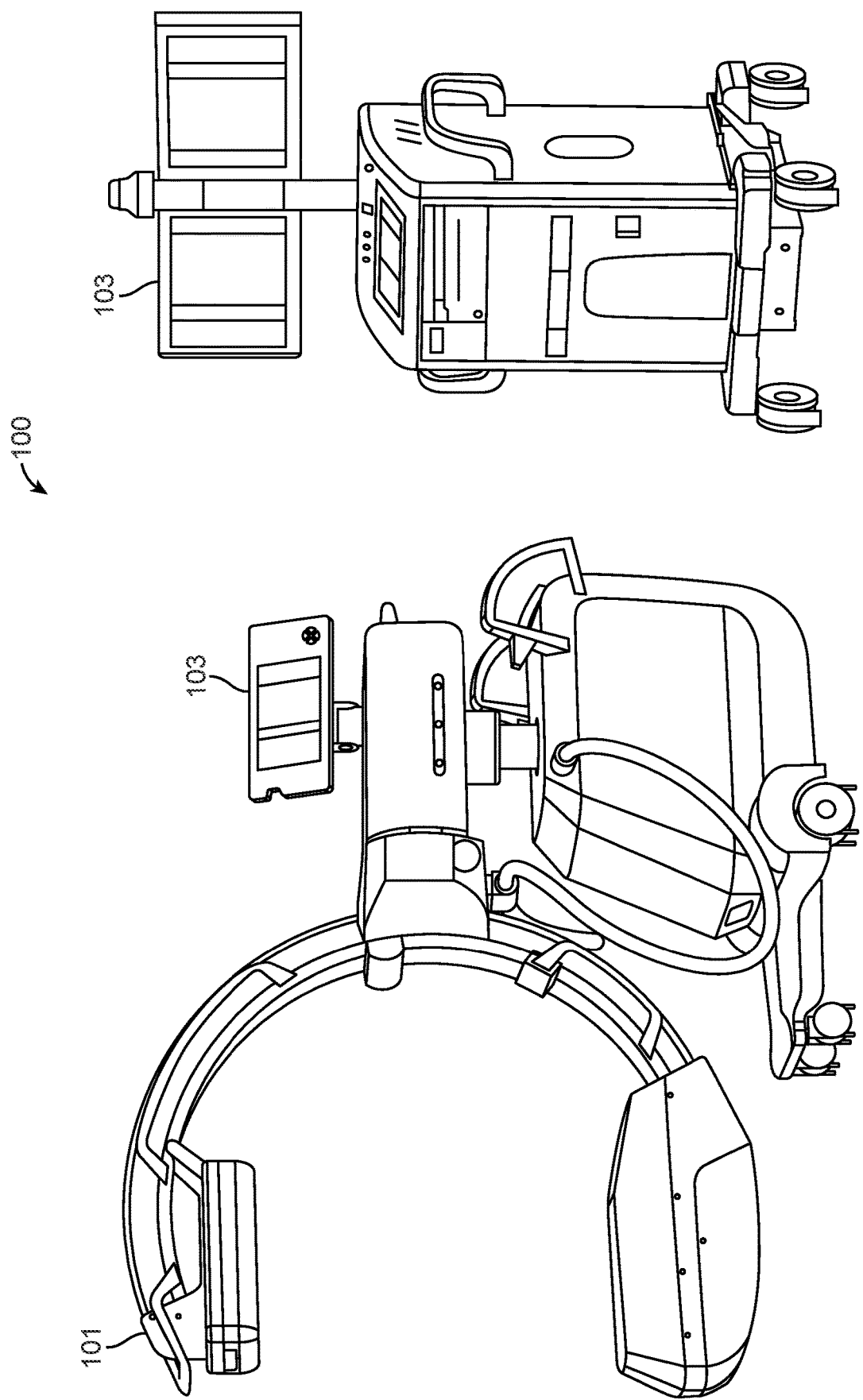
FIG. 1 schematically illustrates an example imaging system, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides systems and methods that are capable of improving live medical video quality. In particular, the provided systems and methods may employ a deep learning framework that can perform real-time video quality enhancement or video denoising during live video acquisition. The deep learning framework for video denoising may dynamically tune the degree of temporal denoising and/or spatial denoising depending on the sequence of input frames and/or the specific application.

In some cases, the deep learning framework may allow the degree of spatial and temporal denoising to vary frame-wise. In some cases, a model may be trained to allow the degree of spatial and temporal denoising vary spatially within each frame. For instance, if an object is moving in a part of an image frame/video (across one or more image frames temporally), the model/algorithm may be able to predict a weight map corresponding to the motion and dynamically adjust the temporal/spatiotemporal denoising according to the weight map. This beneficially allows for performing temporal denoising in the region (and the surrounding regions) based on the motion in the region to mitigate blurring.

The provided systems and methods may enhance video quality in real-time in various aspects. Examples of low quality in live medical imaging may include noise (e.g., low signal noise ratio), low spatial resolution, temporal artifacts (e.g., visible flickering), contrast, blur (e.g., motion artifact), shading (e.g., blockage or interference with sensing), missing information (e.g., missing pixels or voxels due to removal of information or masking), reconstruction (e.g., degradation in the measurement domain), and/or under-sampling artifacts (e.g., under-sampling due to compressed sensing, aliasing).

In some embodiments, the provided deep learning framework may include a two-stage denoising in that a first stage denoising may be performed in the spatial domain (e.g., to mitigate low signal noise ratio, contrast, artifacts, etc.) and a second stage denoising may be performed in the temporal domain or spatiotemporal domain (e.g., to mitigate blur or motion artifact) with a predicted skip weight map (motion map) to tune the degree of the denoising. In some cases, the degree of denoising in the first stage may also be dynamically tuned based on a use application or a property of the input video.

In some cases, the deep learning framework of the provided systems and methods may also be capable of improving the live imaging quality (real-time video denoising) allowing for reduced ionizing radiation exposure. This beneficially allows for reducing the ionizing radiation exposure without compromising the live imaging quality. Systems and methods of the present disclosure can be applied to various live imaging modalities such as fluoroscopic imaging, computed tomography (CT), single photon emission computed tomography (SPECT) scanners, functional magnetic resonance imaging (fMRI), or magnetic resonance imaging (MRI) scanners, Positron Emission Tomography (PET) and various others. Though fluoroscopic imaging and ionizing radiation examples are primarily provided herein, it should be understood that the present approach may be used in other imaging modality contexts where live imaging denoising is desired.

The term "video quality" of surgical imaging may generally refer to the presence of the various live imaging artifacts that may affect the visual effect as described above (e.g., noise, contrast, missing information, low spatial solution, temporal artifacts such as flickering, etc.), or accuracy of imaging (e.g., accuracy of quantitative biomarker assessment). For example, video with high video quality may generally refer to video with low level of video artifacts whereas as low video quality may refer to high level of video artifacts. Various predictors, such as signal to noise ratio (SNR), contrast, sharpness, spatial/temporal resolution and the like, can be employed for qualifying and/or quantifying the video quality.

The term "real-time," as used herein, generally refers to a response time of less than 1 second, tenth of a second, hundredth of a second, a millisecond, or less, such as by a computer processor. Real-time can also refer to a simultaneous or substantially simultaneous occurrence of a first event with respect to occurrence of a second event.

The term "reduced radiation dose" as utilized herein may refer to an amount or level of radiation dose that is lower than the amount/level of radiation dose (e.g., normal/standard radiation dose) which is utilized for live imaging in order to achieve adequate quality in absent of the provided systems and methods. For example, the provided methods and systems may be capable of reducing the radiation dose by at least 10%, 20%, 30%, 40%, 50%, 60%, 70%, 80%, or 90% without lowering the quality the video or live imaging.

The provided systems and methods may be capable of achieving real-time video enhancement by performing image frame enhancement in no more than 60 millisecond, 50 millisecond, 40 millisecond, 30 millisecond, 20 millisecond, at a frame rate of at least 10 frame per second, 20 frame per second, 30 frame per second, 40 frame per second, 50 frame per second, thereby avoiding latency. In some examples, systems and methods of the present disclosure may be capable of achieving real-time video enhancement in no more than 33.3 millisecond or 12 millisecond, at about 30 frames per second (fps) and 1536×1536 image resolution. In some examples, the real-time video enhancement can be achieved at at least 10 fps, 15 fps, 20 fps, 30 fps, 40 fps, 50 fps, 60 fps, 70 fps, 80 fps, 90 fps, 100 fps without decreasing an image resolution of an existing imaging system.

The image resolution may be dependent on the imaging sensor of the imaging system. The imaging sensor may be capable of capturing an image frame or a sequence of image frames at a specific image resolution. The image frame resolution may be defined by the number of pixels in a frame. The image resolution may be greater than or equal to about 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, 1536×1536, or 1536×8640 pixels. The imaging device may be, for example, a 4K camera or a camera with a higher resolution.

The imaging sensor may capture a sequence of image frames at a specific capture rate. In some cases, the sequence of images may be captured at standard fluoroscopic video frame rates such as about 25 frames per second or 30 frames per second. In some cases, the sequence of images may be captured at a rate less than or equal to about the standard frame rate while the temporal resolution of the video may be improved by the present methods and systems (e.g., interpolating across frames for smoother motion or reduce visible flicker).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The provided systems and methods may provide a deep learning framework to allow for dynamic video denoising based on both temporal and spatial information. As described above, the deep learning framework for video denoising may dynamically tune the degree of temporal denoising and/or spatial denoising depending on both the sequence of input frames and the particular application. The term "degree" of denoising may refer to the number of frames (e.g., window size) for temporal averaging, a selection of frames to not perform a denoising operation (e.g., skip selected frames for temporal or spatial denoising), a number of pixels for spatial denoising, and/or various denoising coefficients.

The deep learning framework may allow the degree of spatial and temporal denoising to vary frame-wise. In some embodiments, a model may be trained to enable the degree of spatial and temporal denoising to vary spatially within each frame. For example, if an object is moving in a part of an image frame/video (across one or more consecutive image frames), the model/algorithm may be able to tune the degree of denoising according to the motion. This beneficially allows for minimal temporal denoising in the region (and the surrounding regions) where motion occurs to mitigate blurring.

In some cases, the deep learning framework may allow the degree of spatial denoising to vary as a function of the temporal denoising. For example, the degree of spatial denoising may be inversely related to the degree of spatial denoising. For instance, when motion is presented in a video, the model may apply lower degree of temporal denoising such as by decreasing the averaging window size to mitigate blurring. In some instances, when little motion is presented (e.g., the video is substantially static), the model may perform low degree of spatial denoising such as by decreasing the number of pixels for filtering so as to preserve the spatial resolution.

The provided systems and methods may further beneficially allow for live image acquisition under reduced radiation dose or low radiation exposure with improved video quality. For instance, fluoroscopy is a type of medical imaging that shows a continuous X-ray image on a monitor, much like an X-ray movie. During a fluoroscopy procedure, an X-ray beam is passed through the patient body. The image is transmitted to a display so the movement of a body part or of an instrument or contrast agent ("X-ray dye") through the body can be seen in detail. The radiation dose that the patient receives varies depending on the individual procedure. Fluoroscopy can result in relatively high radiation doses, especially for complex interventional procedures (such as placing stents or other devices inside the body) which require fluoroscopy be administered for a long period of time. Fluoroscopic imaging taken under reduced radiation dose and/or low frame rate (e.g., low temporal resolution) may result in low video quality (e.g., high noise, low resolution, low contrast, visible flicker). Methods and systems of described herein, may improve the quality of the live medical image in real-time while allowing for reduced radiation dose. Methods and systems of the present disclosure can be conveniently integrated or applied to any existing imaging system without requiring modification to the physical system (e.g., hardware configuration or set up).

Methods and systems provided herein may be capable of improving the quality of live medical imaging in real-time by utilizing a deep learning enhancement mechanism. Conventional denoising methods may employ deep learning to improve quality of a single-frame image such as improve resolution in the spatial domain within a single image frame. However, the conventional deep learning methods may not be applicable for live imaging or real-time imaging quality enhancement due to the high runtime for inference. For example, one family of existing solutions for video denoising are patch-based algorithms which construct 3D spatiotemporal volume by tracking blocks along motion trajectories with similar blocks, thus leveraging non-local spatial correlation as a fourth dimension. A second family of existing solutions to video denoising consists of deep learning methods such an end-to-end trained neural network which performs spatial denoising, frame warping, and temporal denoising in subsequent steps. However, the primary issue with both the patch-based and neural network methods is that they require an explicit step of motion estimation or compensation. Performing explicit motion estimation and/or motion compensation can be computationally expensive which prohibit real-time denoising capability. Additionally, current denoising methods may not be capable of adapting to the motion in both spatial and temporal domain.

Methods and systems herein advantageously provide real-time video denoising by employing an improved deep learning framework or deep learning enhancement mechanism. In some embodiments, the deep learning enhancement mechanism may improve live imaging quality by leveraging intraframe information in conjunction with interframe information. The output of the deep learning enhancement mechanism may be image stream with improved quality in at least one of noise, contrast, preserving spatial resolution, and temporal resolution (e.g., smoothing motion dynamically, reducing flickering, interpolating across frames for smoother motion) or other video quality metrics (e.g., Peak Signal-to-Noise Ratio (PSNR), Video Quality Metric (VQM), Structural Similarity index (SSIM), Mean Structural Similarity (MSSIM) index, and Visual Signal-to noise Ratio (VSNR), etc.).

In some embodiments, the deep learning enhancement mechanism may be implemented by a convolutional neural network with rapid video denoising capabilities. In some cases, the enhancement mechanism may comprise a modified U-Net framework such as Fast Deep Video Denoising network (DVDnet). Details about the dynamic denoising or motion resilient denoising mechanism are described later herein.

System Overview

The systems and methods can be implemented on an existing imaging system without a need of a change of hardware infrastructure. FIG. 1 schematically illustrates an example imaging system 100, in accordance with some embodiments. In the illustrated example, the imaging system 100 may comprise an imaging device (e.g., a C arm or O arm fluoroscopic imaging system) 101 to capture intraoperative live images. As described above, though fluoroscopic imaging system is illustrated in the example, the methods can be applied to any other imaging systems where live imaging denoising is desired without being limited to the types of the imaging systems. The imaging device 101 can utilize any suitable imaging modalities for capturing live video of a patient that may involve continuous radiation exposure of the patient and surgeon. The imaging system may be, for example, C-arm image intensifier or O-arm intraoperative CT. For instance, high-resolution X-ray images may be captured by the C-arm imaging scanner 101 in real-time, thus allowing the physician to monitor progress and immediately make any corrections. The C-arm fluoroscopy system may comprise a generator and X-ray image intensifier that converts x-rays into visible light at higher intensity than mere fluorescent screens do. The generator emits X-rays that penetrate the patient's body. The image intensifier or detector converts the X-rays into a visible image displayed on the monitor or other display of the imaging system 103.

In one aspect of the disclosure, a deep learning-based live imaging enhancement system may be provided to an imaging system 100 to improve the quality of the video in real-time. Quality of the live video may be improved in real-time such that the physician or surgeon may view the improved video on the display 103 without time delay.

Figure 2:
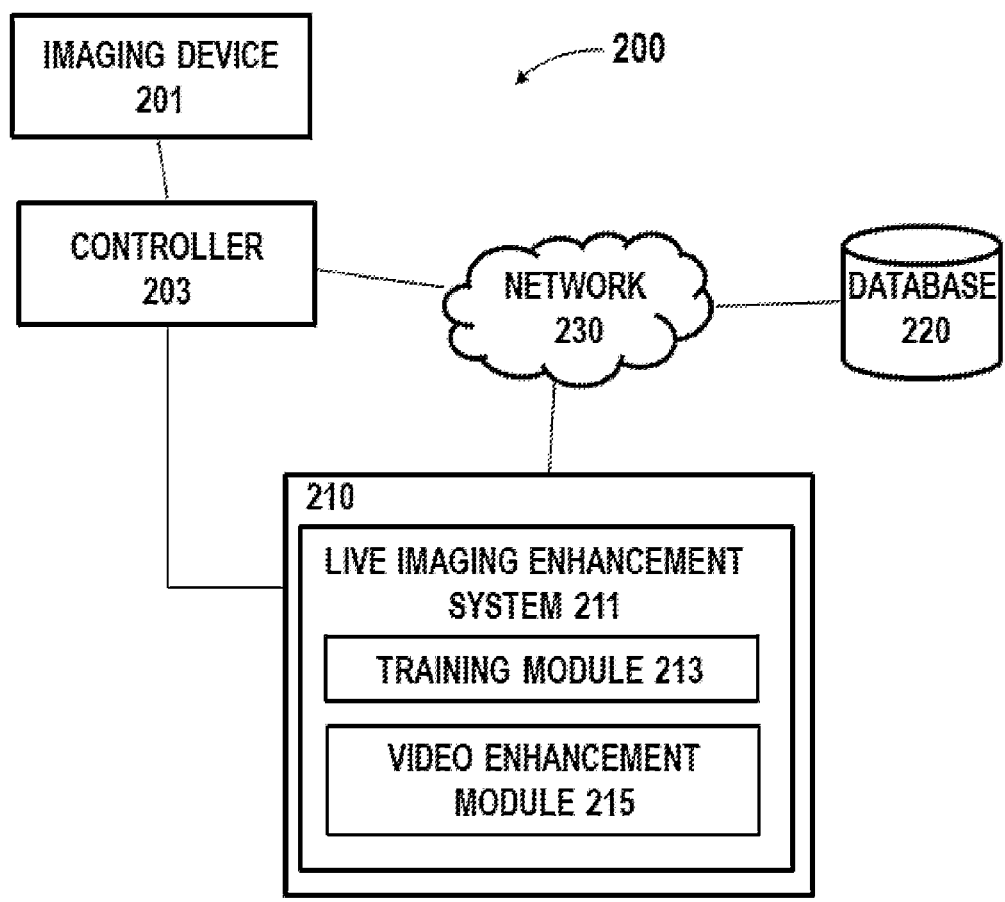
FIG. 2 schematically illustrates a live imaging enhancement system implemented in an imaging platform for real-time video enhancement, in accordance with some embodiments of the disclosure.

FIG. 2 schematically illustrates a live imaging enhancement system 211 implemented on an imaging platform 200 for real-time video enhancement. Video enhancement may be performed in real-time during surgical operations. For instance, quality of image frames may be improved in real-time as image frame being captured by the imaging device 201. Additionally, video enhancement may be performed at any desired time point after a video (or a portion of the video) has been captured.

The imaging platform 200 may comprise a computer system 210 and one or more databases 220 operably coupled to a controller 203 over the network 230. The computer system 210 may be used for implementing the methods and systems consistent with those described elsewhere herein to improve the quality of live video in real-time. The computer system 210 may be used for implementing a live imaging enhancement system 211. The live imaging enhancement system 211 may comprise a training module configured to develop and train a deep learning framework using training datasets and a video enhancement module configured to execute the trained deep learning framework to perform inference. Although the illustrated diagram shows the controller and computer system as separate components, the controller and computer system (at least part of the live imaging enhancement system) can be integrated into a single component.

The imaging device 201 may acquire live video or image frames as described in FIG. 1. Live video or image frames may be streamed in using any medical imaging modality such as but not limited to CT, fMRI, SPECT, PET, ultrasound, etc or any combination of the above. The live imaging enhancement system 211 may process the live video to generally enhance the quality such as by performing denoising in the spatial and temporal domain. In some cases, image quality of the captured live video or image data stream may be degraded due to, for example, low temporal resolution or reduction in radiation dose or presence of noise in imaging sequence. The captured video stream may have a low-quality such as low image resolution (spatial resolution), low temporal resolution, low contrast, or low signal to noise ratio (SNR).

The controller 203 may be in communication with the imaging device 201, one or more displays and the live imaging enhancement system 211. The controller 201 may be operated to provide the controller information to manage the operations of the imaging system, according to installed software programs. For example, the controller 203 may control various components of the imaging system such as X-ray tube, spectral shaping filters, collimator, an anti-scatter grid, an image receptor (X-ray Image Intensifier), digital cameras based on charge-coupled device (CCD) image sensors or complementary metal oxide semiconductor (CMOS) technology, and various other post-image processing components.

In some cases, at least part of the live imaging enhancement system 211 may be integrated to the controller 203 or local to the controller such that video enhancement can be performed locally in real-time. In some cases, the live imaging enhancement system 211 may employ an edge intelligence paradigm such that inference or video enhancement may be performed at the edge or edge gateway (e.g., imaging system). In some instances, deep learning model may be built, developed and trained on a cloud/data center and run on the imaging system (e.g., hardware accelerator). For example, software that run on the edge may be the trained deep learning framework for processing the image stream in real-time. Software that run on the cloud or an on-premises environment may be the training module for training, developing, and managing the deep learning models.

The controller 203 may comprise or be coupled to an operator console which can include input devices (e.g., keyboard) and control panel and a display. For example, the controller may have input/output ports connected to a display, keyboard and other I/O devices. In some cases, the operator console may communicate through the network with a computer system that enables an operator to control the production (e.g., X-ray tube and image receptor) and display of live video on a screen of display. The live video displayed on the display may be processed by the live imaging enhancement system 211 and have improved quality.

The imaging platform 200 may comprise a user interface. The user interface may be configured to receive user input and output information to a user. The user input may be related to controlling or setting up a video acquisition scheme. For example, the user input may indicate radiation dose (e.g., radiation dose level, a dose reduction factor, etc.), frame rate for acquisition, desired radiation exposure level for each acquisition/run. In some cases, the user input may be related to the video enhancement algorithm (e.g., sliding window size, estimated motion or property of a video, etc.) or desired enhancement parameters such as video smoothing level or sharpness level. The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

In some cases, the user interface may comprise a graphical user interface (GUI) allowing a user to select an operation mode, video displaying parameters, video enhancement parameters and image acquisition settings as described elsewhere herein. In some embodiments, the live imaging enhancement system 211 may allow for different operation modes. In some cases, the different operation modes may comprise at least a live video denoising mode, and a retrospective mode where a captured video is processed by the live imaging enhancement system 211 at a delayed time (e.g., after a complete video is captured or after at least part of a video is captured). The graphical user interface may allow a user to input user command to switch between the two operation modes.

The GUI may show graphical elements that permit a user to view or access information related to video enhancement or video display. A graphical user interface can have various interactive elements such as buttons, text boxes and the like, which may allow a user to provide input commands or contents by directly typing, clicking or dragging such interactive elements.

In some cases, the graphical user interface (GUI) or user interface may be provided on a display. The display may or may not be a touchscreen. The display may be a light-emitting diode (LED) screen, organic light-emitting diode (OLED) screen, liquid crystal display (LCD) screen, plasma screen, or any other type of screen. The display may be configured to show a user interface (UI) or a graphical user interface (GUI) rendered through an application (e.g., via an application programming interface (API) executed on the local computer system or on the cloud). The display may be on a user device, or a display of the imaging system as described in FIG. 1.

The live imaging enhancement system 211 may comprise multiple components such as a training module 213 configured to develop and train a deep learning framework using training datasets, and a video enhancement module 215 for deploying the trained deep learning framework and performing inferences. In some cases, the live imaging enhancement system may further be configured for continual training, generating and preparing training datasets, and managing deep learning models.

The training module 213 may be configured to train a deep learning model. In some embodiments, the training module may be configured to train a plurality of deep learning models assembled in a layered architecture (e.g., two-stage hierarchy) for enhancing video quality in real-time. The training module may train the plurality of deep learning models individually. Alternatively or in addition to, the plurality of deep learning models may be trained as an integral model.

The training module 213 may be configured to generate and manage training datasets. For example, the training datasets for the real-time video enhancement may comprise pairs of low quality (e.g., low-dose) video and high quality (e.g., high-dose) video or 'ground-truth' video. In some cases, the high quality video may have a quality equal to or higher than a video acquired at a standard radiation dose. The videos may contain a moving object such that the model can be trained to denoise or reduce the artifacts caused by the movement.

High quality medical video datasets can be rare. Paired videos from the same subject can be even harder to collect. In some cases, the provided training module may implement proprietary algorithm to simulate low-quality video and/or high-quality video to generate pairs of training datasets. For instance, video data taken under standard radiation dose (e.g., from clinical database) may be processed to generate high-quality video data simulating a high radiation dose (e.g., by applying temporal averaging and denoising to the standard video data). The same standard video data may also be processed to create a low-quality video data simulating low radiation dose by introducing artifacts to the video data such as by adding simulated noise scaled at different levels to the video data. In some cases, the noise may be introduced to simulate blurring caused by a moving object in the video.

The training module 213 may be configured to train a deep learning network for enhancing the image quality. For example, the training module may employ supervised training, unsupervised training or semi-supervised training techniques for training the model. The training module may be configured to implement the machine learning methods as described elsewhere herein. The training module may train a model off-line. Alternatively or additionally, the training module may use real-time data or newly collected data as feedback to refine the model for improvement or continual training.

The video enhancement module 215 may be configured to enhance video quality in real-time using a trained model provided by the training module. The video enhancement module may implement the trained model for making inferences in real-time, i.e., producing image frames with improved quality. Details about the deep learning model architecture and model framework are described with respect to FIGS. 3-6.

The computer system 210 may be programmed or otherwise configured to manage and/or implement the video enhancement module, training module and its operations. The computer system 210 may be programmed to implement methods consistent with the disclosure herein.

The imaging platform 200 may comprise computer systems 210 and database systems 220, which may interact with the live imaging enhancement system 211. The computer system may comprise a laptop computer, a desktop computer, a central server, distributed computing system, etc. The processor may be a hardware processor such as a central processing unit (CPU), a graphic processing unit (GPU), a general-purpose processing unit, which can be a single core or multi core processor, or a plurality of processors for parallel processing. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

The computer system 210 can communicate with one or more remote computer systems through the network 230. For instance, the computer system 210 can communicate with a remote computer system of a user or a participating platform (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 210 or the live imaging enhancement system via the network 230.

The imaging platform 200 may comprise one or more databases 220. The one or more databases 220 may utilize any suitable database techniques. For instance, structured query language (SQL) or "NoSQL" database may be utilized for storing video data, collected raw data, enhanced video data, training datasets, trained model (e.g., hyper parameters), user specified parameters (e.g., window size), etc. Some of the databases may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present disclosure is implemented as a data-structure, the use of the database of the present disclosure may be integrated into another component such as the component of the present disclosure. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The network 230 may establish connections among the components in the imaging platform and a connection of the imaging system to external systems. The network 230 may comprise any combination of local area and/or wide area networks using both wireless and/or wired communication systems. For example, the network 230 may include the Internet, as well as mobile telephone networks. In one embodiment, the network 230 uses standard communications technologies and/or protocols. Hence, the network 230 may include links using technologies such as Ethernet, 802.11, worldwide interoperability for microwave access (WiMAX), 2G/3G/4G/5G mobile communications protocols, asynchronous transfer mode (ATM), InfiniBand, PCI Express Advanced Switching, etc. Other networking protocols used on the network 230 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), and the like. The data exchanged over the network can be represented using technologies and/or formats including image data in binary form (e.g., Portable Networks Graphics (PNG)), the hypertext markup language (HTML), the extensible markup language (XML), etc. In addition, all or some of links can be encrypted using conventional encryption technologies such as secure sockets layers (SSL), transport layer security (TLS), Internet Protocol security (IPsec), etc. In another embodiment, the entities on the network can use custom and/or dedicated data communications technologies instead of, or in addition to, the ones described above.

Deep Learning Framework

Figure 3:
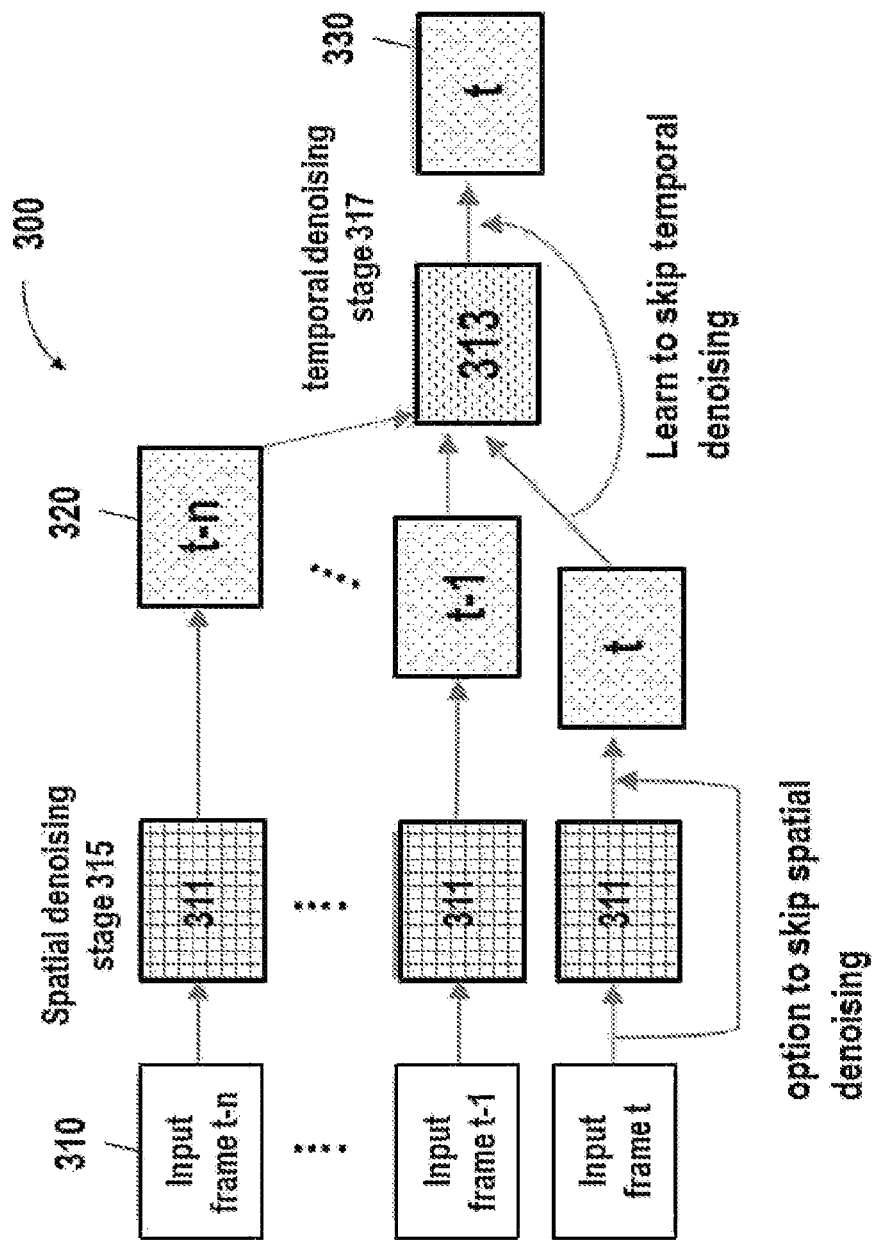
FIG. 3 schematically illustrates the architecture of the deep learning enhancement system, in accordance with some embodiments of the invention.

FIG. 3 schematically illustrates the architecture of a deep learning enhancement system 300, in accordance with some embodiments of the invention. The deep learning enhancement system 300 can be the same as the video enhancement module as described in FIG. 2. The deep learning enhancement system may comprise a trained deep learning model that is capable of improving live video quality or performing dynamic denoising. In some embodiments, the deep learning enhancement system may comprise a plurality of functional blocks. In some cases, each functional block may comprise a modified U-net model 311, 313. In some embodiments, the deep learning architecture may comprise a series of components that are used to improve the input image frames quality (e.g., denoising video).

In some embodiments, the input of the deep learning framework 310 may comprise low-quality image data stream, and the output of the deep learning framework 330 may comprise an image frame with improved quality. In the illustrated example, a series of consecutive image frames 310 may be processed by the deep learning framework 300 to generate an image frame 330 (e.g., estimation of the center frame of the series of input frames) with improved quality. Live video enhancement may be achieved by performing denoising with varied degree in both spatial and temporal domain. This unique architecture may beneficially provide a dynamic spatiotemporal denoiser with a built-in learning process without performing an additional, explicit motion estimation or compensation.

In some cases, the deep learning framework 300 may comprise serialized functional blocks. The serialized functional blocks may be configured to perform spatial denoising in a first stage 315 and temporal denoising in a second stage 317. In some cases, spatiotemporal denoising may be performed in the second stage 317. Each input frame from a series of consecutive frames 310 may be spatially denoised individually in the first stage 315. The output of the first stage 320 may then be fed to a spatiotemporal denoiser or a temporal denoiser 313 in the second stage 317.

For instance, a plurality of functional blocks 311 (e.g., Denoising block) in the first stage 315 may be used to process a series of consecutive image frames 310. In some cases, the first set of functional blocks 311 may share the same weights. The series of consecutive image frames 310 may be from an image stream or live imaging. In some embodiments, the number of functional blocks or arrangement of the functional blocks of the first stage may depend on a sliding window size n (e.g., number of consecutive image frames being processed in order to output one final output image frame 330).

In some cases, each functional block 311 of the first stage may receive and process one input frame from the consecutive image frames 310. For instance, a first denoising block 311 may receive a frame t-n and denoise the frame t-n spatially. The output of a functional block in the first stage may be an intermediate image frame 310 with quality enhanced in the spatial domain.

The first stage of image frame enhancement may denoise the input images in the spatial domain. The output of the functional blocks in the first stage may be a series of intermediate image frames 320 (e.g., n intermediate image frames) with enhanced quality over the original input image frames in the spatial domain.

In some cases, the first stage denoising may be dynamically adjusted based on use applications. For example, a degree of spatial denoising may be dynamically adjusted based on a motion, tissue movement, moving object, patient motion, surgical operation and the like captured in the input video. In some embodiments, the degree of spatial denoising may be based on a property of the video, surgical operation, imaging modality and real-time conditions. For instance, spatial denoising may be skipped for selected frames or regions within a frame based on different surgical operations, different time points during surgical operations and/or for different portions of an image frame (e.g., subset of pixels, patches in an image frame). In some cases, the degree of spatial denoising (e.g., whether to apply spatial denoising to certain frames) may be dynamically adjusted based on a motion estimation in the video. For instance, spatial denoising may be skipped for selected frames when little motion is detected in those frames to preserve spatial resolution. For instance, when the input video is substantially static, the degree of spatial denoising may be reduced to preserve spatial resolution. In some cases, such motion characteristics may be provided to the system prior to the processing. For instance, a user may input a use application related to the video indicating whether the video is likely to be static or contains moving object. Alternatively or additionally, such motion characteristics may be predicted based on the processing of previous image frames in the video. The motion characteristics may be manually provided by a user or automatically adjusted. For instance, an algorithm for motion estimation such as DeepFlow, Farneback algorithm or LiteFlowNet may be applied to the live video to estimate motion at a point in time and/or location of patches (e.g., x, y coordinates) within an image frame, then the degree of spatial denoising may be automatically adjusted (e.g., perform or skip the spatial denoising). In some cases, such dynamic adjustment and/or motion estimation is an inherent part of the deep learning architecture without user input.

The first layer of functional blocks (e.g., denoising block 1 311) may process a series of consecutive image frames substantially in parallel and the output of the first layer of functional blocks may comprise a series of improved image frames 310 to be processed by a functional block (e.g., denoising block 313) in a second stage 317. The denoising block 313 may be a model trained to perform temporal denoising. Alternatively, the denoising block 313 may be model trained to perform spatiotemporal denoising.

In some embodiments, each denoising component (e.g., denoising block 311, denoising block 313) may have a modified U-net architecture. As an example, the modified U-net may be a modified n-layer U-net taking three adjacent frames as input. In some cases, the plurality of denoising blocks in the first stage may have the same modified U-net architecture but the weights may be different. Alternatively, the multiple denoising blocks in the first stage may share the same set of weights. In some cases, a different U-net architecture or number of layers may be selected with respect to different number of input frames. Alternatively, the architecture of the modified U-net may be the same regardless of the number of input frames i.e., sliding window size. Details about the modified U-net architecture are described with respect to FIGS. 4-6.

Figure 4:
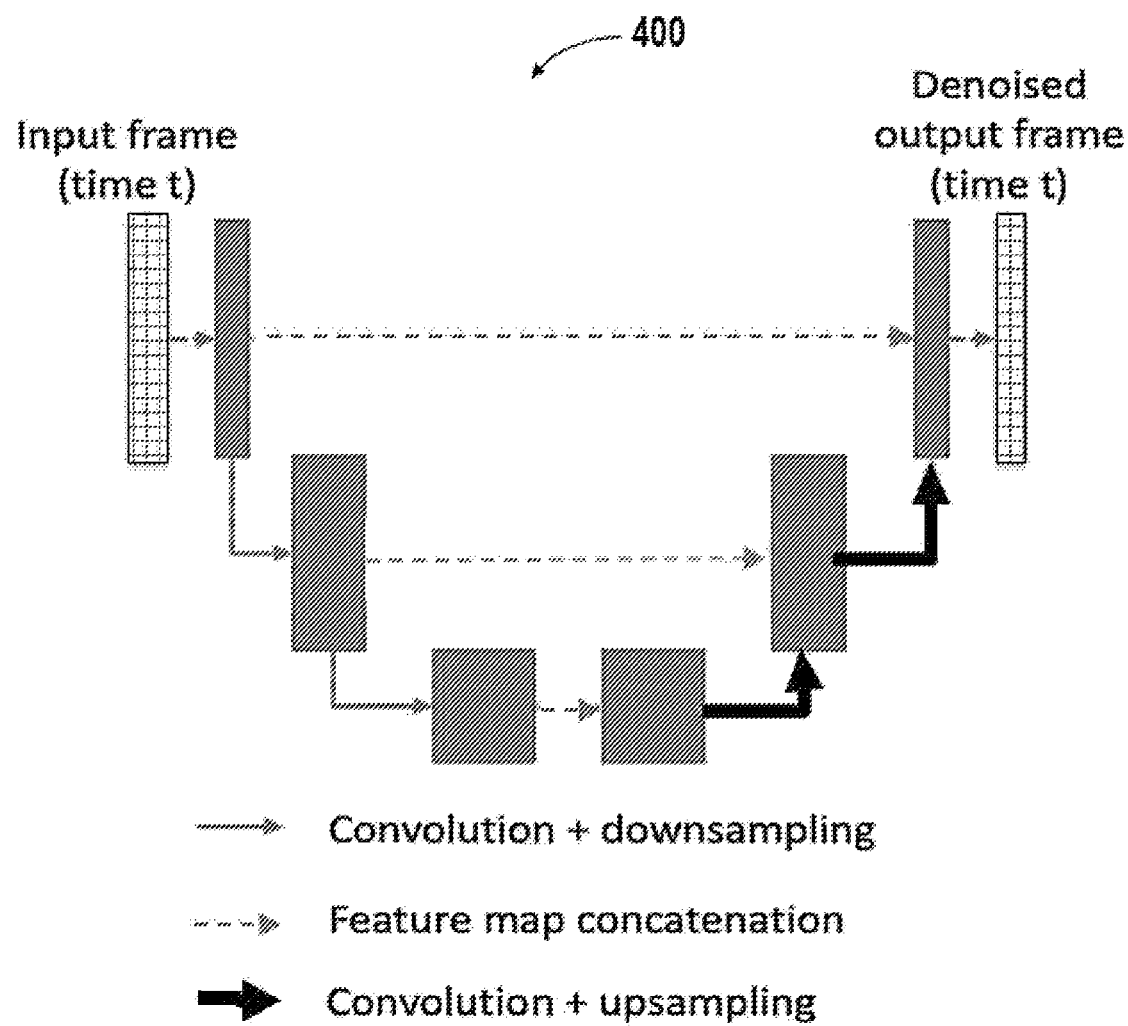
FIG. 4 and FIG. 5 show an example of a modified U-net architecture for a functional block.
Figure 5:
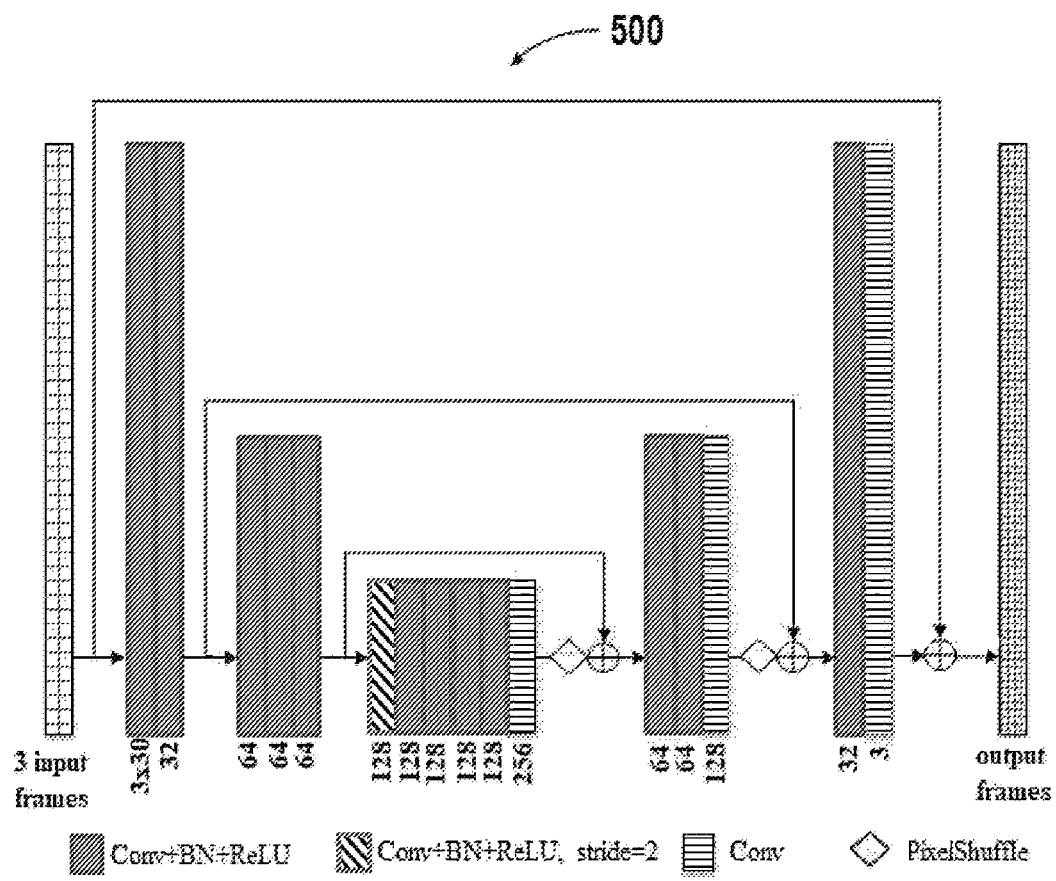

FIG. 4 and FIG. 5 shows an example of a modified U-net architecture 400, 500 for a functional block in the first stage. In some cases, a functional block in the second stage may comprise the same U-net architecture as the first stage. The U-net architecture 400, 500 is essentially a multi-scale encoder-decoder architecture, with skip-connections that forward the output of each of the encoder layers directly to the input of the corresponding decoder layers. In some cases, each functional block or the denoising block in the first stage and the second stage may comprise a modified U-Net. In the illustrated example of the modified U-net architecture, upsampling in the decoder is performed with a pixel shuffle layer which helps reducing gridding artifacts. The merging of the features of the encoder with those of the decoder is performed with pixel-wise addition operation resulting in a reduction of memory requirements. The residual connection between the central noisy input frame and the output frame is introduced to accelerate the training process.

In the illustrated example, a functional block may comprise a plurality of convolutional layers. In most layers, the outputs of the convolutional layers are followed by pointwise ReLU activation functions ReLU(•)=max(•, 0), except for the last layer. At training time, batch normalization layers (BN) are placed between the convolutional and ReLU layers. At evaluation/inference time, the batch normalization layers are removed, and replaced by an affine layer that applies the learned normalization.

Referring back to FIG. 3, the second stage functional block may take the output of the first stage (e.g., intermediate frames 320) as input data and output a final image frame 330 (output frame t) with improved quality. For example, the spatiotemporal network may comprise a multi-channel input with n-timesteps frames inputted as separate channels. The output of the denoising block 313 is the estimate of the central input frame (e.g., Input frame t−n/2) with a quality further improved other the intermediate frames 320. Alternatively, the output of the denoising block may be assigned time index t corresponding to a frame chosen at random such that 2<t≤n−2, wherein n is the total number of frames for a given sample.

The number of input channels (i.e., sliding window size of n) for the denoising block in the second stage may be determined based on a property of the input image stream. The number of input channels of the denoising block in the second stage 313 may or may not be the same as the sliding window size of the input image stream 310 in the first stage. In some cases, the number of input channels (i.e., sliding window size of n) for the denoising block in the second stage matches the number of denoising blocks in the first stage or the sliding window size for the first stage and second stage is the same. Alternatively, the number of input channels (i.e., sliding window size of n) for the denoising block in the second stage may be adjusted/tuned independent of the number of denoising blocks in the first stage.

In some embodiments, the sliding window size of the input image stream to be processed by the deep learning framework may be selected according to a property of the video, surgical operation, imaging modality and real-time conditions. In some embodiments, different sliding window sizes (of temporal neighboring frames) may be dynamically selected for different surgical operations, different time points during surgical operations and/or for different portions of an image frame (e.g., subset of pixels, patches in an image frame). For example, the sliding window size may be dynamically adjusted based on a motion estimation in the video. For instance, smaller window size may be selected when greater motion is detected to mitigate motion blur. In another example, a portion of an image frame (i.e., subset of pixels, patches) may be averaged over fewer adjacent consecutive images (i.e., smaller window size) if a motion is detected within the location of the patch of the image frame. By requiring a small set of consecutive input frames (e.g., ten frames, nine frames, eight frames, seven frames, six frames, five frames, four frames, three frames, etc.) for inference, the denoising method is capable of running in a streaming fashion throughout the video acquisition process without delay.

The parameters for determining input data stream such as the sliding window size may be manually selected by a user or automatically adjusted. For instance, an algorithm for motion estimation such as DeepFlow, Farneback algorithm or LiteFlowNet may be applied to the live video to estimate motion at a point in time and/or location of patches within an image frame, then window size for processing the input image stream or a selected patch of the image frame may be automatically adjusted.

Figure 6A:
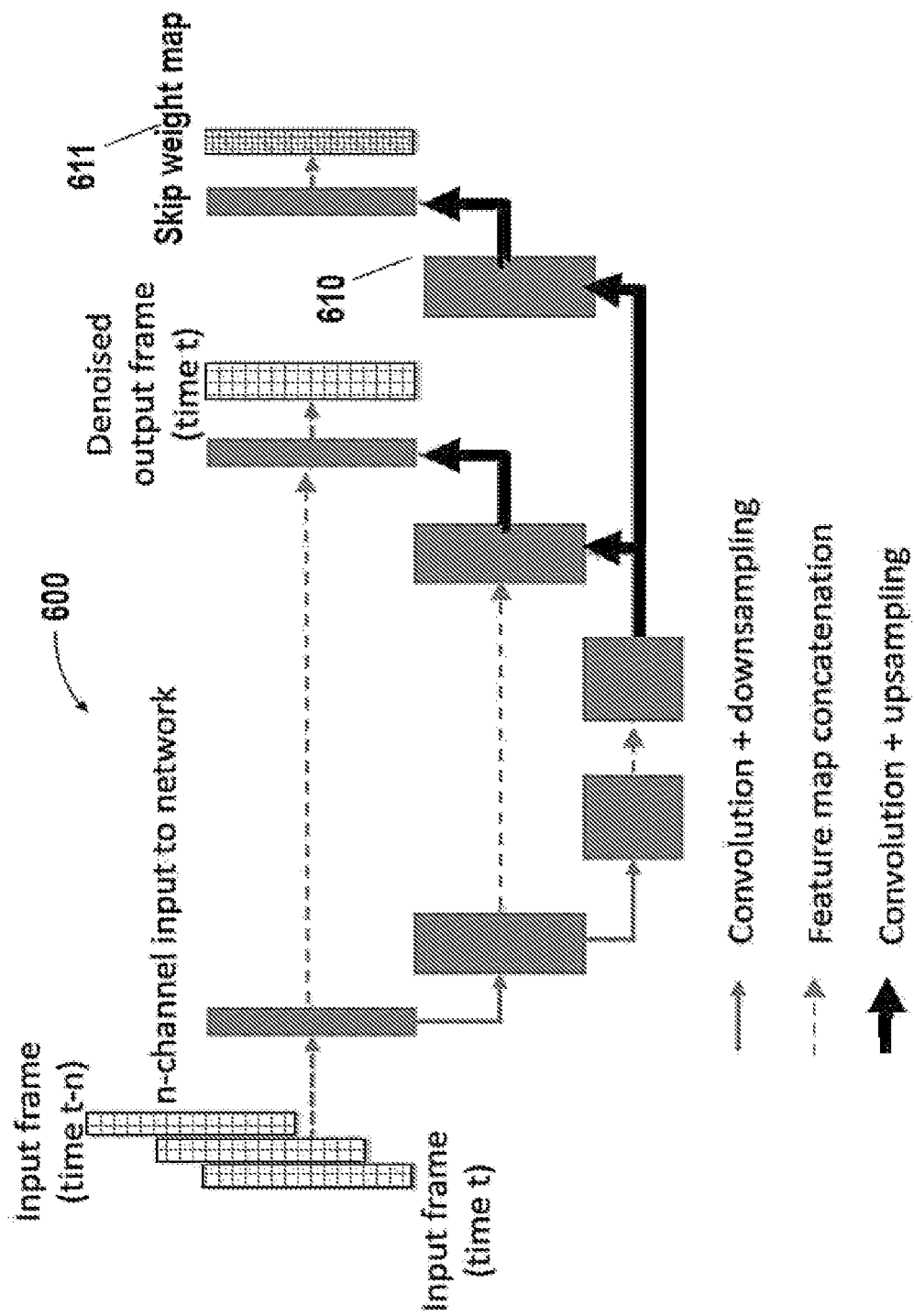
FIG. 6A and FIG. 6B shows an example of a denoising network in a second stage.

In some cases, the dynamic adjustment of the window size and/or motion estimation is an inherent part of the deep learning architecture. The temporal denoiser or spatiotemporal denoiser 313 may include a multi-channel denoising network with inherent motion estimation capability. For example, the network may be trained to predict a skip weight map indicating or corresponding to the regions of motion in the input frame sequence. The term "skip weight map" may also be referred to as "motion map" which are used interchangeably throughout the specification. A sliding window size may be decreased for the region within an image frame where motion is predicted in the skip weight map. In some embodiments, the denoising network may comprise a separate network for predicting a skip weight map. FIG. 6A shows an example of denoising network 600 in the second stage. In some embodiments, the denoising network 600 may comprise a multi-task temporal or spatiotemporal network. The multi-task temporal or spatiotemporal network may comprise an integral component 610 for predicting a skip weight map 611. The multi-task temporal or spatiotemporal network may be an integrated network that the component for predicting a skip weight map and the component for performing the temporal denoising are trained concurrently.

Figure 6B:
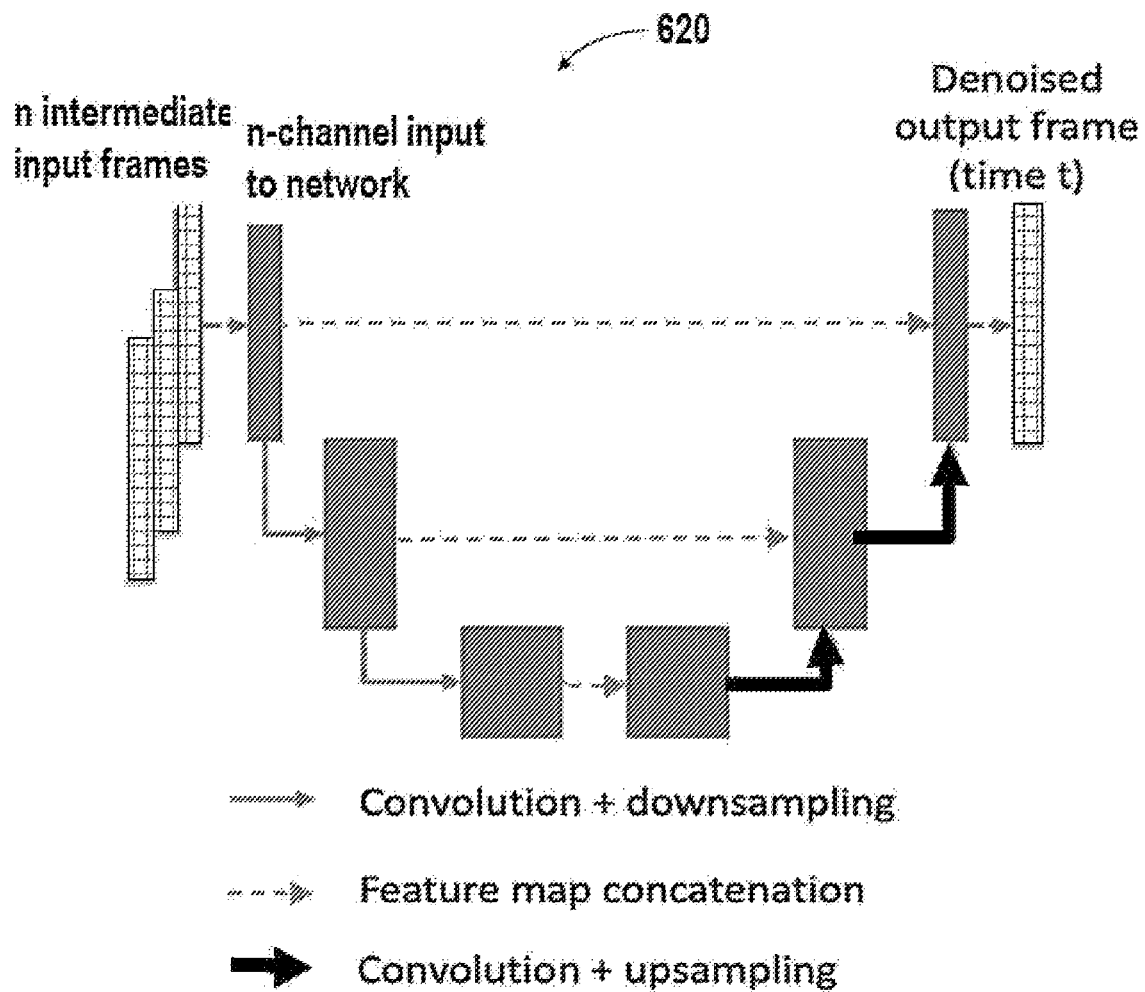

In alternative embodiments, the network in the second stage may comprise a separate network (not shown) trained to predict skip weight map and a network 610 that performs temporal (or denoising network) denoising and generate a final output based at least in part on the skip weight map. FIG. 6B shows an example of a denoising network 620 in the second stage. The denoising network 620 may be trained to apply temporal or spatiotemporal denoising to the plurality of intermediate input frames based on the skip weight map predicted by a separate network and output a final output frame. The denoising network in the second stage may have a U-net architecture that is substantially the same as the U-net architecture as described above.

Figure 7:
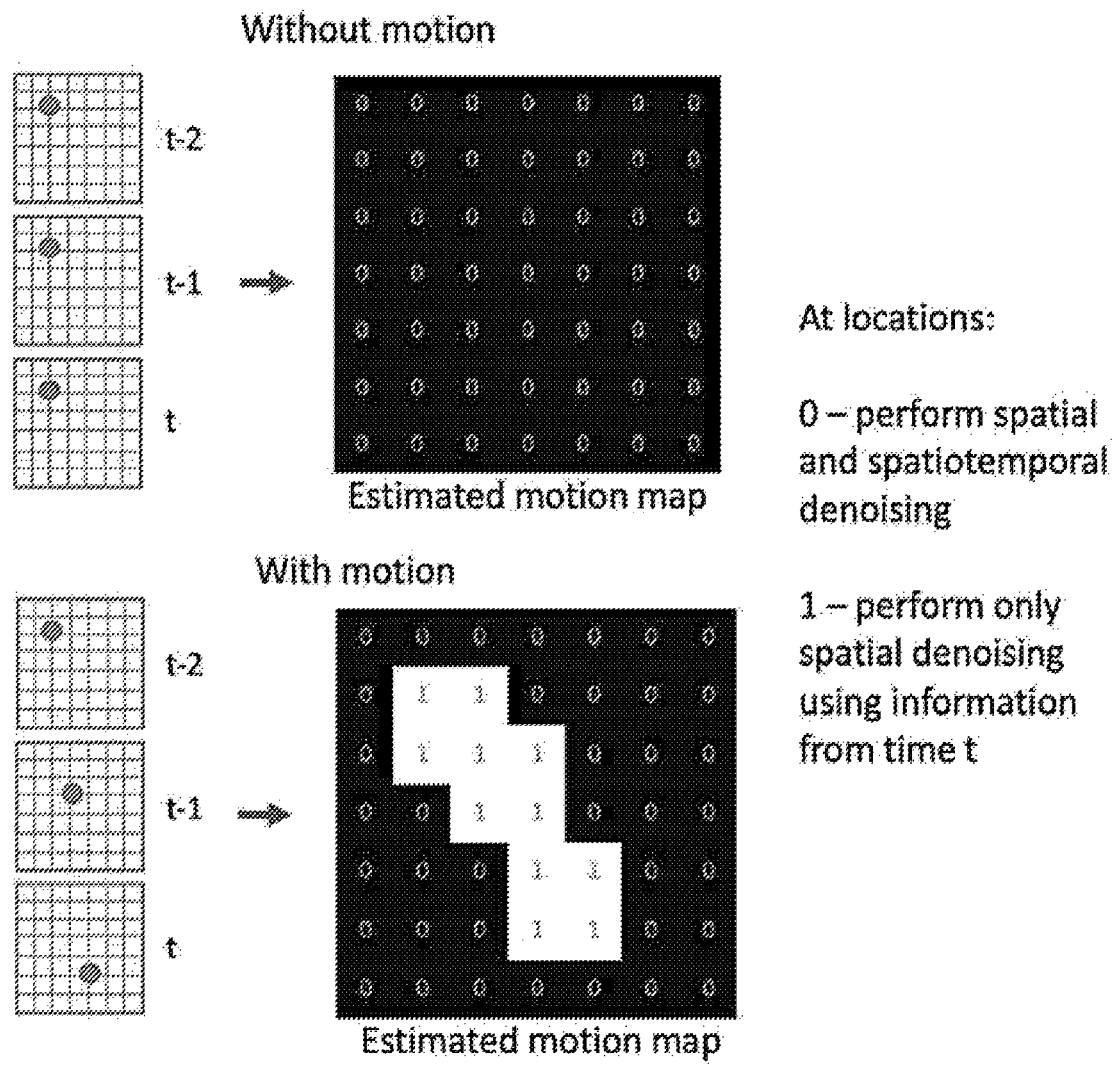
FIG. 7 shows an example of a skip weight map generated by the denoising network in the second stage.

The denoising network may be trained to perform temporal (or denoising network) denoising as well as predict a skip weight or a skip weight map. The skip weight map may indicate or correspond to the regions of motion in the input frame sequence. FIG. 7 shows an example of a skip weight map generated by the denoising network in the second stage. As shown in the example, the skip weight map may have the same spatial resolution as the input image frame and the value for each pixel may indicate motion corresponding to that pixel. In some cases, a value/weight for a pixel may indicate whether performing temporal denoising to the pixel or not. For example, as shown in the figure, a value/weight of zero may indicate performing temporal and spatiotemporal denoising on the input n image frames, a value/weight of 1 may indicate performing only spatial denoising to each individual image frame without temporal denoising. The skip weight map can be in any form (in addition to binary). For example, the value/weight for a pixel may be any value between zero and one or any number indicating a sliding window size for performing the temporal denoising.

The denoising network 600, 620 for the temporal or spatiotemporal denoising may classify whether individual pixels contain motion based on the sequence of input frames (e.g., re-channel input to the network). The denoising network may predict the location in which objects are moving and ensure that there is minimal temporal denoising in these regions thereby preventing blurring due to motion. The skip weight map may be used for localized skipping of the spatiotemporal denoising stage. This is advantageous when motion occurs in only part of the image frame/video.

In some embodiments, the skip weight map may be used to generate a final output image frame. In some embodiments, the skip weight (or skip weight map) may be used to weight the intermediate output (i.e., spatially denoised image frames as output of the first stage) with respect to the spatiotemporally denoised output in the second stage using a linear combination. Below is an example of combining the output from the first stage and output from the second stage to generate a final output image frame:

$$I_{ij}(t \ldots t-n) = w_{ij} \cdot I_{spatial\ ij}(t) + (1-w_{ij}) I_{spatiotemporal\ ij}(t \ldots t-n)$$

where $I_{ij}$ is the final output at time t at pixel ij, $I_{spatial\ ij}$ is the spatially denoised output at ij, $I_{spatiotemporal\ ij}$ is the spatiotemporally denoised output, $w_{ij}$ is the skip weight at pixel ij of the weight map and n is the number of time steps used for spatiotemporal denoising. It should be noted that the intermediate image frames and the spatiotemporally denoised frame can be combined using various other equations (e.g., linear, non-linear combination).

The deep learning model can employ any type of neural network model, such as a feedforward neural network, radial basis function network, recurrent neural network, convolutional neural network, deep residual learning network and the like. In some embodiments, the deep learning algorithm may be convolutional neural network (CNN). The model network may be a deep learning network such as CNN that may comprise multiple layers. For example, the CNN model may comprise at least an input layer, a number of hidden layers and an output layer. A CNN model may comprise any total number of layers, and any number of hidden layers. The simplest architecture of a neural network starts with an input layer followed by a sequence of intermediate or hidden layers, and ends with output layer. The hidden or intermediate layers may act as learnable feature extractors, while the output layer may output the improved image frame. Each layer of the neural network may comprise a number of neurons (or nodes). A neuron receives input that comes either directly from the input data (e.g., low quality image data etc.) or the output of other neurons, and performs a specific operation, e.g., summation. In some cases, a connection from an input to a neuron is associated with a weight (or weighting factor). In some cases, the neuron may sum up the products of all pairs of inputs and their associated weights. In some cases, the weighted sum is offset with a bias. In some cases, the output of a neuron may be gated using a threshold or activation function. The activation function may be linear or non-linear. The activation function may be, for example, a rectified linear unit (ReLU) activation function or other functions such as saturating hyperbolic tangent, identity, binary step, logistic, arcTan, softsign, parameteric rectified linear unit, exponential linear unit, softPlus, bent identity, softExponential, Sinusoid, Sinc, Gaussian, sigmoid functions, or any combination thereof. During a training process, the weights or parameters of the CNN are tuned to approximate the ground truth data thereby learning a mapping from low-quality video (e.g., low-dose video) to high-quality video (e.g., ground-truth video).

Model Training and Development

In some embodiments, the deep learning model may be trained using supervised learning. For example, in order to train the deep learning network, pairs of videos with low quality and high-quality videos as ground truth may be generated by the training module of the system as training dataset. In some embodiments, the training datasets may comprise simulated low-quality video and/or high-quality video with motion in the video. The low-quality videos may comprise videos acquired under lower radiation dose, shorter acquisition time or with blurring caused by motion in the video. In some embodiments, the low-quality videos may comprise simulated low-quality videos generated from videos taken at standard radiation dose as described above. For instance, a video taken at standard radiation dose may be used to simulate a high-quality video and one or more low-quality videos (e.g., by adding noise scaled at different or selected levels, or introducing different types of artifacts). In some cases, video data taken under standard radiation dose (e.g., from clinical database) or standard acquisition time may be processed to generate high-quality video data simulating a high radiation dose (e.g., by applying temporal averaging and denoising to the standard video data). The same standard video data may also be processed to generate low-quality video data simulating low radiation dose by introducing selected types of artifacts to the video data and/or adding noise at different levels, e.g., adding noise scaled at different levels, to the video data.

The training datasets for training the model in the first stage (e.g., spatial denoiser) and the model in the second stage (e.g., temporal/spatiotemporal denoiser) may be different. For example, the low quality videos used for training the spatial denoiser may simulate spatial artifacts whereas the low quality videos for the temporal or spatiotemporal denoiser may simulate artifacts in the temporal or spatiotemporal domain (e.g., visible flickering, motion blur, etc.).

In some embodiments, the part or component of the second stage denoising network that estimates the skip weight or skip weight map may be trained in a supervised fashion. For example, a ground-truth weight map and a loss function may be used for training the network. The ground-truth weight map may consist of a map of regions where a motion exists. For example, the region with or without motion may be represented by a weight such as a binary gate, or any value between zero and one. The spatiotemporal denoiser network may act as a motion detector network and may be trained in a multi-task fashion that performs both spatiotemporal denoising and predicting a skip weight map such as shown in FIG. 6B. Alternatively, the network for predicting the skip weight map may be trained as a separate network such as shown in FIG. 6A.

In some embodiments, the deep learning model for enhancing video quality in real-time may be trained using supervised learning. Training datasets generated by the aforementioned method may be utilized to train the deep learning model or various components of the deep learning model. For example, the training dataset may comprise pairs of ground truth frame and a small set of noisy frames (corresponding to a sliding window size) as described above. An example of the loss function for model training may be following:

$$L(\theta) = L_1(\tilde{f}_t^p, \hat{f}_t^p) = \|\tilde{f}_t^p - F(X_t^p; \theta)\|_1$$

Wherein $\hat{f}_t^p = F(X_t; \theta)$ is the output of the network F parameterized by $\theta$. $\tilde{f}_t$ is the ground truth at time t, and $X_t = \{f_{t-2}, f_{t-1}, f_t, f_{t+1}, f_{t+2}\}$ which is a consecutive set of noisy, low-quality image frames. The patch index p may be a selected patch dimension. For example, the patch dimension may be 256×256 or any other number. The time index t corresponds to a frame chosen at random such that 2<t≤T−

2, wherein T is the total number of frames for a given sample. It should be noted that the L1 loss is an example of the loss function. Various other loss functions such as SSIM or perceptual loss may be utilized in various, different scenarios.

In some embodiments, the deep learning model may be trained using unsupervised learning or semi-supervised learning that may not require abundant labeled data. High quality medical image datasets or paired dataset can be hard to collect. In some cases, the provided method may utilize unsupervised training approach allowing the deep learning method to perform continual training and apply on existing datasets (e.g., unpaired dataset) that are already available in clinical database. In some embodiments, the training process of the deep learning model may employ residual learning method. In some cases, the network structure can be a combination of U-net structure and a residual network.

In some embodiments, the model training process may further comprise operations such as model pruning and compression to improve inference speed. Model tuning may comprise deleting nodes of the trained neural network that may not affect network output. Model compression may comprise using lower precision network weights such as using floating point 16 instead of 32. This may beneficially allow for real-time inference (e.g., at high inference speed) while preserving model performance.

Example

Figure 8:
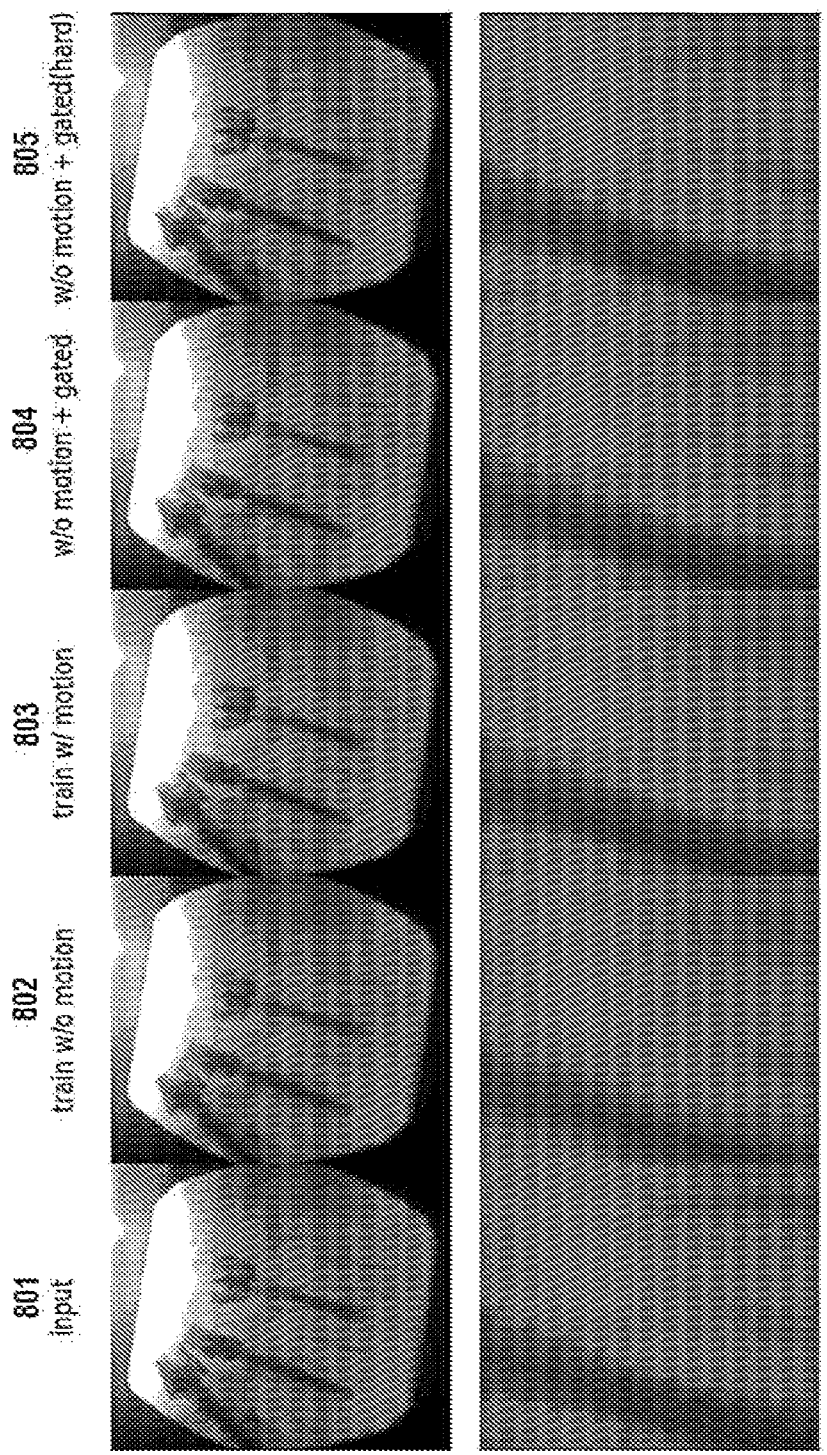
FIG. 8 shows an example of an image frame from a live video with low image equality, and an improved image frame produced by the deep learning enhancement system.

FIG. 8 shows an example of an image frame from a live video with low video quality 801, and an improved image frame 803 produced by the deep learning enhancement system.

In the example, the individual frame from input video 801 is proceed by the deep learning models. When the input image frame is processed using the denoiser that is trained without motion in the input data and the skip weight map is employed (i.e. a model detects there is motion in this sequence of frames), the output image frame 804 is generated as a linear combination of the spatially denoised video frame (from the first stage) and the spatiotemporal stage (second stage). The final output image frame 804 exhibits significantly reduced blurring compared to the spatiotemporal denoiser trained without motion on input data 802 or the spatiotemporal denoiser trained with motion but without skip weight map 803. The output image frame 804 is generated using a non-binary skip weight map. When a binary skip weight map is employed, the final output image is shown as 805 which also demonstrated reduced blurring.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for improving live video quality comprising:
    (a) receiving a stream of consecutive image frames of a subject, wherein the stream of consecutive image frames are acquired using a medical imaging apparatus; and
    (b) processing the stream of consecutive image frames using a two-stage deep learning framework by:
        i) feeding the stream of consecutive image frames to a first set of denoising components in a first stage of the two-stage deep learning framework, wherein at least one of the first set of denoising components comprises a first deep learning network trained to denoise an image frame in a spatial domain by taking as input an image frame from the stream of consecutive image frames and predicting an intermediate image frame;
        ii) feeding a plurality of the intermediate image frames to a second denoising component in a second stage of the two-stage deep learning framework, wherein the second denoising component comprises a second deep learning network trained to predict a final image frame with improved quality in both temporal domain and spatial domain based at least in part on a predicted motion map which motion map indicating a presence of motion in the plurality of the intermediate image frames.

2. The computer-implemented method of claim 1, wherein the second deep learning network is an integrated multi-task network trained to predict the motion map and perform temporal or spatiotemporal denoising.

3. The computer-implemented method of claim 1, wherein the second denoising component comprises a network separate from the second deep learning network and wherein the network is trained to predict the motion map.

4. The computer-implemented method of claim 1, further comprising combining of the plurality of intermediate image frames and a denoised image frame generated by the second denoising component using the motion map to output the final image frame.

5. The computer-implemented method of claim 1, wherein the motion map is a binary map and has a spatial resolution same as the intermediate image frame.

6. The computer-implemented method of claim 5, wherein a value of a pixel in the motion map indicates whether to perform temporal or spatiotemporal denoising to the pixel.

7. The computer-implemented method of claim 1, wherein a number of the stream of consecutive image frames are adjustable.

8. The computer-implemented method of claim 1, wherein the medical imaging apparatus is performing fluoroscopic imaging.

9. The computer-implemented method of claim 1, wherein the stream of consecutive image frames is acquired with a reduced amount of radiation dose.

10. The computer-implemented method of claim 1, wherein the first deep learning network or the second deep learning network includes a modified U-net model.

11. The computer-implemented method of claim 1, wherein the first deep learning network is trained using training datasets comprising a pair of a simulated low-quality video and a simulated high-quality video.

12. The computer-implemented method of claim 11, wherein the simulated low-quality video comprises a motion of an object.

13. The computer-implemented method of claim 11, wherein the pair of the simulated low-quality video and the simulated high-quality video are generated from a video acquired at a standard amount of radiation dose.

14. The computer-implemented method of claim 13, wherein the simulated low-quality video is generated by introducing a selected type of artifact or a simulated noise at a selected level to the video acquired at the standard amount of radiation dose.

15. A system for improving live video quality comprising:
(i) a communication interface communicatively coupled to a medical imaging apparatus, (ii) a memory for storing a set of software instructions, and (iii) one or more processors configured to execute the set of software instructions to:
(a) receive, from the medical imaging apparatus, a stream of consecutive image frames of a subject; and
(b) process the stream of consecutive image frames using a two-stage deep learning framework by:
  i) feed the stream of consecutive image frames to a first set of denoising components in a first stage of the two-stage deep learning framework, wherein at least one of the first set of denoising components comprises a first deep learning network trained to denoise an image frame in a spatial domain by taking as input an image frame from the stream of consecutive image frames and predicting an intermediate image frame;
  ii) feed a plurality of the intermediate image frames to a second denoising component in a second stage of the two-stage deep learning framework, wherein the second denoising component comprises a second deep learning network trained to predict a final image frame with improved quality in both temporal domain and spatial domain based at least in part on a predicted motion map which motion map indicating a presence of motion in the plurality of the intermediate image frames.

16. The system of claim 15, wherein the second deep learning network is an integrated multi-task network trained to predict the motion map and perform temporal or spatiotemporal denoising.

17. The system of claim 15, wherein the second denoising component comprises a network separate from the second deep learning network and wherein the network is trained to predict the motion map.

18. The system of claim 15, where the one or more processors are configured to further combine of the plurality of intermediate image frames and a denoised image frame generated by the second denoising component using the motion map to output the final image frame.

19. The system of claim 15, wherein the motion map is a binary map and has a spatial resolution same as the intermediate image frame.

20. The system of claim 19, wherein a value of a pixel in the motion map indicates whether to perform temporal or spatiotemporal denoising to the pixel.

* * * * *